(12) United States Patent
Levin et al.

(10) Patent No.: US 12,036,049 B1
(45) Date of Patent: Jul. 16, 2024

(54) STORAGE SYSTEM WITH TRAYS FOR LONG MEDICAL IMPLANTS

(71) Applicant: DEPUY SYNTHES PRODUCTS, INC., Raynham, MA (US)

(72) Inventors: Aron Levin, Pottsdown, PA (US); Simon Scherrer, Zurich (CH); Henri Defossez, Neuchatel (CH); Scott Jacobs, Glenmoore, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 18/167,321

(22) Filed: Feb. 10, 2023

(51) Int. Cl.
*A61B 50/22* (2016.01)
*A61B 50/00* (2016.01)

(52) U.S. Cl.
CPC ...... *A61B 50/22* (2016.02); *A61B 2050/0074* (2016.02)

(58) Field of Classification Search
CPC ......... A61B 50/22; A61B 50/30; A61B 50/33; A61B 50/34; A61B 50/3006; A61B 50/3007; A61B 50/3008; A61B 50/3011; A61B 50/3014; A61B 50/3015; A61B 2050/005; A61B 2050/0051; A61B 2050/0052; A61B 2050/0053; A61B 2050/0054; A61B 2050/0055; A61B 2050/0056; A61B 2050/0057; A61B 2050/0058; A61B 2050/0059; A61B 2050/006; A61B 2050/0061; A61B 2050/0062; A61B 2050/0063; A61B 2050/0064; A61B 2050/0074; B25H 3/003; B25H 3/04; B25H 3/06; B25H 3/02; B25H 3/021; B25H 3/023; B25H 3/027; B25H 3/028
See application file for complete search history.

(56) References Cited

U.S. PATENT DOCUMENTS

| 2,286,427 | A | * | 6/1942 | Levensten | ................ B25H 3/02 312/902 |
| 4,135,868 | A |   | 1/1979 | Schainholz | |
| 4,267,939 | A |   | 5/1981 | Perrett | |

(Continued)

FOREIGN PATENT DOCUMENTS

| DE | 29714090 U1 * | 10/1997 | ............. A61B 50/20 |
| DE | 102006016866 A1 * | 10/2007 | ........... A61B 17/865 |

(Continued)

*Primary Examiner* — Stanton L Krycinski
(74) *Attorney, Agent, or Firm* — Kramer & Amado, P.C.

(57) ABSTRACT

A storage system, including: a lid; a bottom side of the storage system opposite the lid; a first plurality of medical implants stored in a rack, wherein first plurality of medical implants are oriented in a first direction from the lid to the bottom side; a first drawer located between a portion of the first plurality of medical implants and the bottom side of the storage system; a second plurality of medical implants stored in the first drawer, wherein the second plurality of medical implants are oriented in a second direction that is substantially perpendicular to the first direction; and a drawer locking mechanism configured to engage the first drawer when the lid is closed to prevent the first drawer from sliding out of the storage system and to disengage the first drawer when the lid is open to allow the first drawer to slide out of the storage system.

20 Claims, 15 Drawing Sheets

(56) References Cited

U.S. PATENT DOCUMENTS

| | | | |
|---|---|---|---|
| 4,643,494 A * | 2/1987 | Marleau | A45C 5/00 |
| | | | 292/120 |
| 4,659,154 A * | 4/1987 | Jenkins | A01K 97/26 |
| | | | 312/277 |
| 4,662,515 A * | 5/1987 | Newby, Sr. | B25H 3/02 |
| | | | 312/258 |
| 4,978,510 A | 12/1990 | Smith | |
| 5,174,453 A * | 12/1992 | Stoeffler | A61B 50/33 |
| | | | 206/439 |
| 5,176,419 A * | 1/1993 | Guerdet | B25H 3/023 |
| | | | 294/146 |
| 5,215,726 A | 6/1993 | Kudla | |
| 5,294,413 A | 3/1994 | Riihimaki | |
| 5,492,671 A | 2/1996 | Krafft | |
| 5,603,559 A * | 2/1997 | Yemini | B25H 3/06 |
| | | | 312/334.44 |
| 5,628,970 A | 5/1997 | Basile | |
| 5,725,096 A * | 3/1998 | Winnard | B25H 3/028 |
| | | | 211/DIG. 1 |
| 5,732,821 A | 3/1998 | Stone | |
| 5,738,423 A * | 4/1998 | Alfaro | B25H 1/12 |
| | | | 312/249.11 |
| 5,882,612 A | 3/1999 | Riley | |
| 5,893,618 A * | 4/1999 | LePage, Jr. | A61B 50/22 |
| | | | 312/265.6 |
| 6,099,812 A | 8/2000 | Allen | |
| 6,112,896 A * | 9/2000 | Bal | B30B 15/0082 |
| | | | 220/23.6 |
| 6,116,452 A | 9/2000 | Hamel | |
| 6,158,437 A | 12/2000 | Vagley | |
| 6,164,738 A | 12/2000 | Dane | |
| 6,331,280 B1 | 12/2001 | Wood | |
| 6,579,503 B1 | 6/2003 | Tanamal | |
| 6,713,029 B1 | 3/2004 | Krafft | |
| 6,736,265 B2 * | 5/2004 | Kipper | B25H 3/028 |
| | | | 206/811 |
| 6,783,004 B1 * | 8/2004 | Rinner | A61B 17/8875 |
| | | | 206/370 |
| 6,866,147 B2 | 3/2005 | Barwick | |
| 6,874,634 B2 | 4/2005 | Riley | |
| 6,969,498 B1 | 11/2005 | Riley | |
| 7,523,827 B2 | 4/2009 | Dane | |
| 7,748,529 B2 | 7/2010 | Foreman | |
| 8,061,517 B2 * | 11/2011 | Loeffler | A61B 90/94 |
| | | | 206/347 |
| 8,100,281 B2 | 1/2012 | Sands | |
| 8,685,068 B2 * | 4/2014 | Sixto | A61B 50/30 |
| | | | 606/915 |
| 9,107,502 B2 * | 8/2015 | Heede | A61B 50/20 |
| 9,149,336 B2 | 10/2015 | Dane | |
| 9,198,811 B2 * | 12/2015 | Pizzato | A61F 17/00 |
| 9,314,542 B2 | 4/2016 | Bohnhoff | |
| 9,757,489 B2 | 9/2017 | Allen | |
| 9,844,264 B1 * | 12/2017 | Stewart, III | A47B 87/005 |
| 10,022,464 B2 | 7/2018 | Sarphati | |
| 10,182,628 B2 * | 1/2019 | Tonelli | A45C 13/02 |
| 10,512,517 B2 * | 12/2019 | Orr | B65D 43/163 |
| 10,940,022 B2 | 3/2021 | Stoller | |
| 10,945,804 B2 | 3/2021 | Matityahu | |
| 11,110,591 B2 * | 9/2021 | Chen | B25H 3/028 |
| 11,147,896 B2 | 10/2021 | Lucier | A61L 2/206 |
| 11,229,497 B2 * | 1/2022 | Schwartzbauer | A61B 50/34 |
| D952,900 S | 5/2022 | Rosin | |
| 11,325,242 B1 * | 5/2022 | Chen | B25H 3/022 |
| 11,491,248 B2 | 11/2022 | Rhodes | |
| 2006/0124486 A1 * | 6/2006 | Faust, III | A61B 50/31 |
| | | | 206/363 |
| 2008/0067095 A1 * | 3/2008 | Mueller | B25H 3/023 |
| | | | 206/372 |
| 2010/0065456 A1 * | 3/2010 | Junk | A61L 2/26 |
| | | | 206/363 |
| 2012/0234781 A1 * | 9/2012 | Cogliano | B25H 3/06 |
| | | | 211/85.13 |
| 2019/0039233 A1 * | 2/2019 | Liu | B25H 3/028 |
| 2020/0289682 A1 | 9/2020 | Rhodes | |
| 2021/0186673 A1 | 6/2021 | Stoller | |
| 2021/0259797 A1 | 8/2021 | Gorz | |
| 2022/0096674 A1 | 3/2022 | Hu | |
| 2022/0125603 A1 | 4/2022 | Huff | |
| 2022/0371176 A1 * | 11/2022 | Yang | B25H 3/028 |

FOREIGN PATENT DOCUMENTS

| | | | | |
|---|---|---|---|---|
| DE | 102009052838 A1 * | 5/2011 | | A61B 17/865 |
| EP | 1839683 A1 * | 10/2007 | | A61B 50/22 |
| GB | 673093 A * | 6/1952 | | |
| GB | 2501102 A * | 10/2013 | | A61B 50/22 |

* cited by examiner

STORAGE SYSTEM WITH TRAYS FOR LONG MEDICAL IMPLANTS

FIELD OF THE DISCLOSURE

Various exemplary embodiments disclosed herein relate to storage system with an implant rack and trays for long medical implants.

BACKGROUND

Surgical procedures may require a wide variety of surgical implants, for example screws. The screws may be stored in a storage system with a rack. The rack may include a plurality of holes into which screws or other implants are inserted. These screws hang from the rack and extend towards the bottom of the storage system. The storage system may store dozens or even hundreds of screws and other implants with various sizes including different diameters and lengths. Further, various types of screws may be needed for different applications. Therefore, the number of screws and other implements needed for any surgical procedure can quickly multiply. The storage system provides a compact and organized way to store the screws so that a surgical team can quickly and easily obtain the screws needed for the procedure based upon the specific needs of the patient and the procedure.

SUMMARY

A summary of various exemplary embodiments is presented below.

Various embodiments relate to a storage system, including: a lid; a bottom side of the storage system opposite the lid; a first plurality of medical implants stored in a rack, wherein first plurality of medical implants are oriented in a first direction from the lid to the bottom side, and wherein the rack is between the lid and the bottom side of the storage system; a first drawer located between a portion of the first plurality of medical implants and the bottom side of the storage system, wherein the first drawer is configured to slide into and out of the storage system; a second plurality of medical implants stored in the first drawer, wherein the second plurality of medical implants are oriented in a second direction that is substantially perpendicular to the first direction; and a drawer locking mechanism configured to engage the first drawer when the lid is closed to prevent the first drawer from sliding out of the storage system and to disengage the first drawer when the lid is open to allow the first drawer to slide out of the storage system.

Various embodiments are described, including: a second drawer located between the first drawer and the bottom side of the storage system.

Various embodiments are described, wherein one of the first drawer and the second drawer have a tab and the other of the first drawer and the second drawer have a notch, wherein the tab and the notch are configured to engage one another to fix a position of the first drawer and the second drawer relative to one another.

Various embodiments are described, wherein the drawer locking mechanism includes: a drawer latch configured to engage the lid and the first drawer; and a biasing mechanism configured to bias the drawer latch towards the lid.

Various embodiments are described, wherein the biasing mechanism is a leaf spring.

Various embodiments are described, wherein the leaf spring has an opening configured to receive the drawer latch.

Various embodiments are described, wherein the leaf spring has a fork opening configured to engage the drawer latch.

Various embodiments are described, further including: a medical implant loading assembly including: a medical implant loading base configured to receive an end of a medical implant; and rack medical implant loading hole aligned with the medical implant loading base, wherein the rack medical implant loading hole is configured to receive and secure the medical implant along with the medical implant loading base.

Various embodiments are described, where in the first drawer includes a drawer slot and a drawer slot opening on a bottom of the drawer slot at one end of the drawer slot.

Various embodiments are described, where in the first drawer includes a drawer slot and a separator configured to separate medical devices in the drawer slot.

Further various embodiments relate to a storage system, including: a lid configured to be opened and closed; a bottom side of the storage system opposite the lid; a rack between the lid and the bottom side of the storage system, wherein the rack includes a plurality of rack screw holes; a first plurality of screws stored in the plurality of rack screw holes; a first drawer located between a portion of the first plurality of screws and the bottom side of the storage system, wherein the first drawer is configured to slide into and out of the storage system; a second plurality of screws stored in the first drawer, wherein the second plurality of screws are oriented in a direction that is different than a direction of the first plurality of screws; and a drawer locking mechanism configured to engage the first drawer when the lid is closed to prevent the first drawer from sliding out of the storage system and to disengage the first drawer when the lid is open to allow the first drawer to slide out of the storage system.

Various embodiments are described, including: a second drawer located between the first drawer and the bottom side of the storage system.

Various embodiments are described, wherein one of the first drawer and the second drawer have a tab and the other of the first drawer and the second drawer have a notch, wherein the tab and the notch are located to engage one another to fix a position of the first drawer and the second drawer relative to one another.

Various embodiments are described, wherein the drawer locking mechanism includes: a drawer latch configured to engage the lid and the first drawer; and a biasing mechanism configured to bias the drawer latch towards the lid.

Various embodiments are described, wherein the biasing mechanism is a leaf spring.

Various embodiments are described, wherein the leaf spring has an opening configured to receive the drawer latch.

Various embodiments are described, wherein the leaf spring has a fork opening configured to engage the drawer latch.

Various embodiments are described, further including: a screw loading assembly including: a screw loading base configured to receive an end of a screw; and rack screw loading hole aligned with the screw loading base, wherein the rack screw loading hole is configured to receive and secure the screw along with the screw loading base.

Various embodiments are described, where in the first drawer includes a drawer slot and a drawer slot opening on a bottom of the drawer slot at one end of the drawer slot.

Various embodiments are described, where in the first drawer includes a drawer slot and a separator configured to separate medical devices in the drawer slot.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, both their organization and method of operation, together with associated advantages will be better understood from the following description when considered in connection with the accompanying figures. Each of the figures is provided for the purposes of illustration and description, and not as a definition of the limits of the claims.

BRIEF DESCRIPTION OF DRAWINGS

So that the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects. The same reference numbers in different drawings may identify the same or similar elements.

DETAILED DESCRIPTION

Figure 1A:
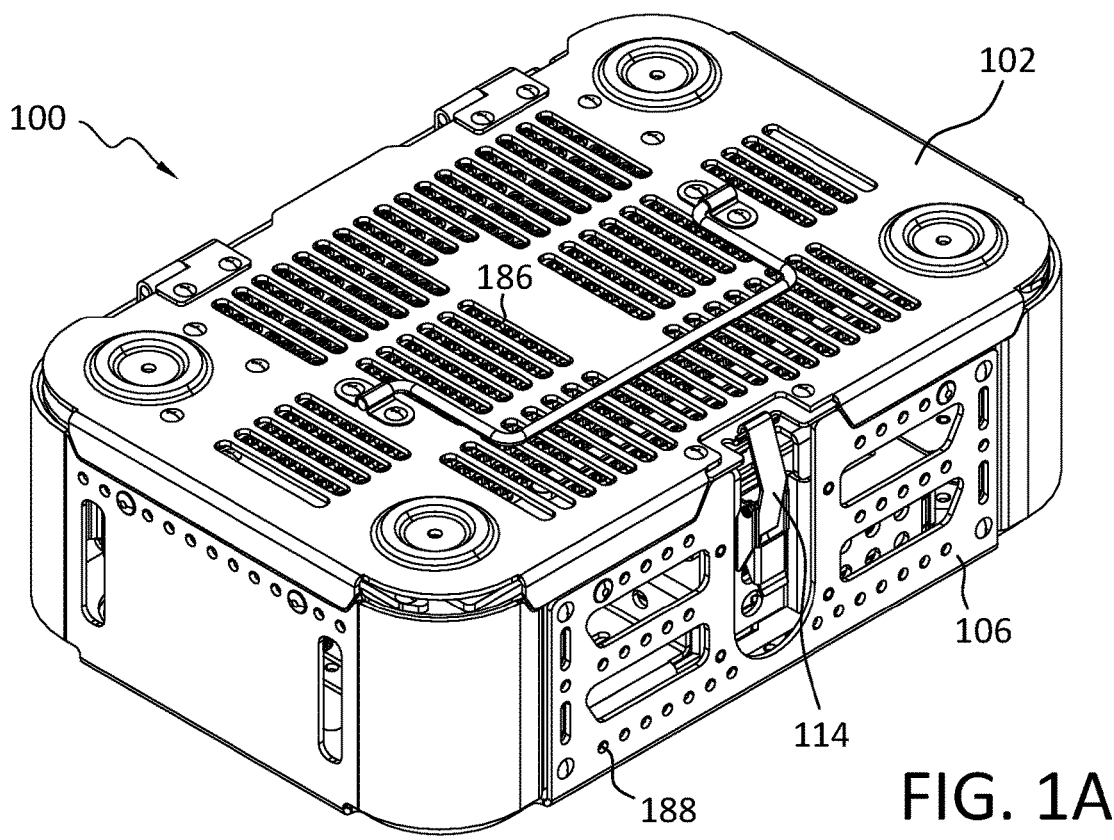
FIGS. 1A-1E illustrate top perspective, top, drawer side, latch side, and bottom perspective view of a storage system.
Figure 1B:
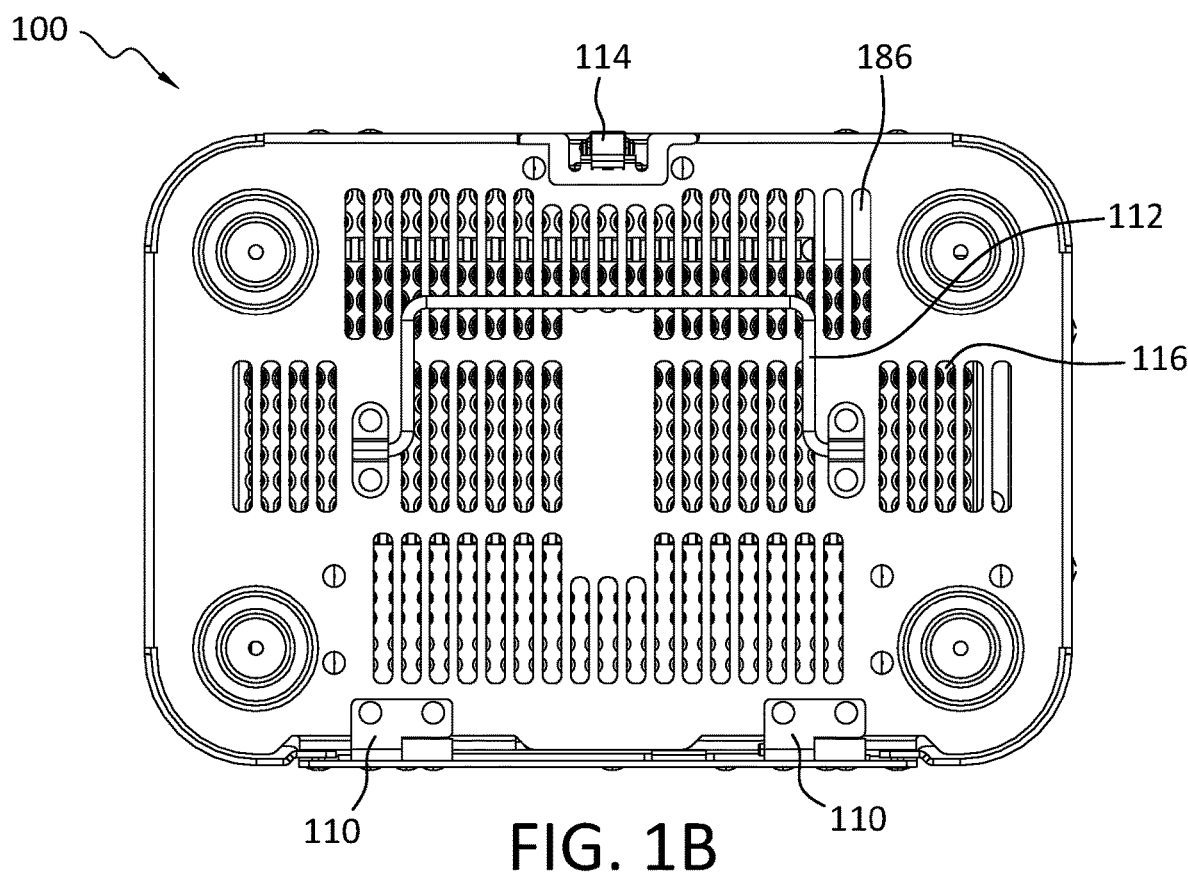
Figure 1C:
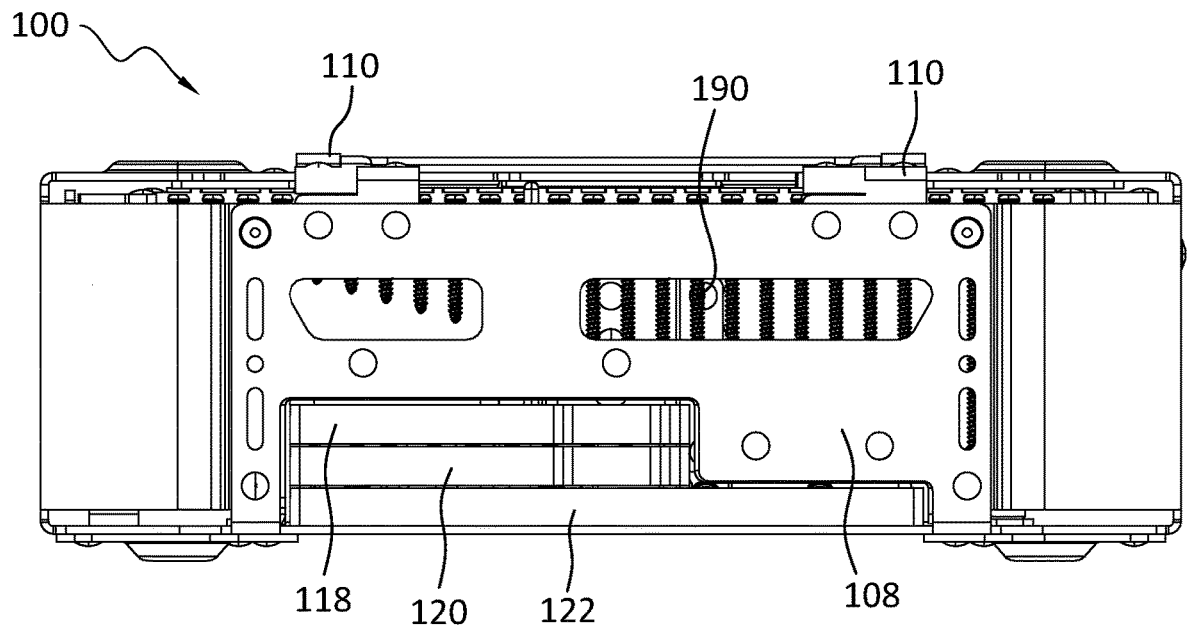
Figure 1D:
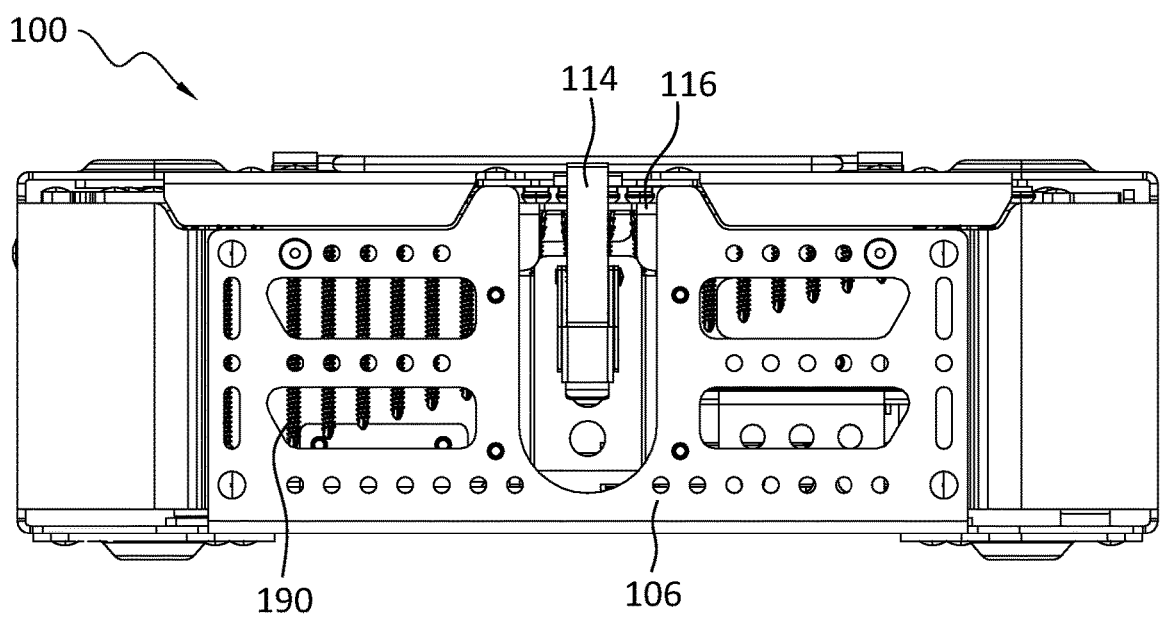
Figure 1E:
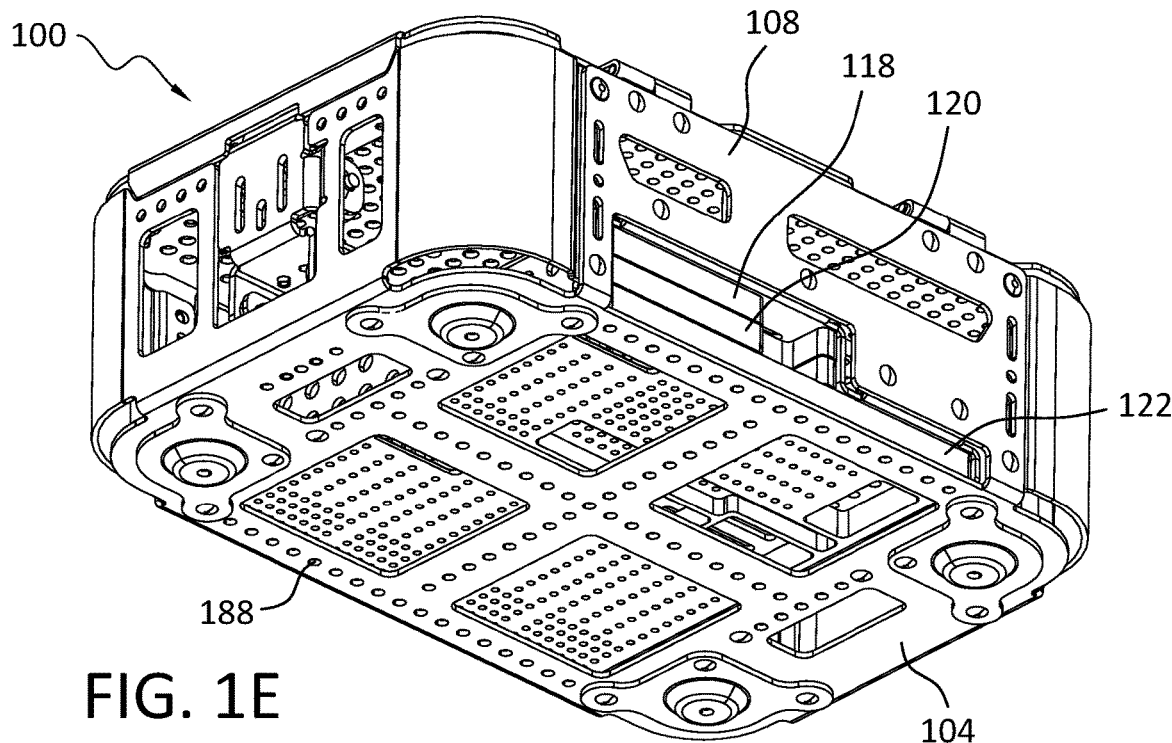

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

Several aspects of medical device storage systems will now be presented with reference to various apparatuses and techniques. These apparatuses and techniques will be described in the following detailed description and illustrated in the accompanying drawings by various blocks, modules, components, steps, processes, and/or the like (collectively referred to as "elements").

Surgical procedures often use various medical implants. This is especially true for orthopedic surgery, where screws, plates, and other implants may be used during a surgical procedure. Because of variations in the treatment of trauma and in the patient anatomy, a wide variety and large number of implants such as screws may be needed to carry out orthopedic surgical procedures. For example, screws may come in a variety of lengths, diameters, materials, and types. Many screws may be required to carry out the surgical procedure. As a result storage systems have been developed that compactly store a wide variety of screws of different sizes, materials, and types. Further, other types of medical implants may be included as well. Also, various instruments needed to carry out the surgical procedure may be included in the storage system in certain applications as well.

In the description of the embodiments of a storage system described herein, for convenience, the focus will be on a storage system that stores screws, as this is a very common need for orthopedic surgeries. The aspects of the embodiments may be expanded to include other types of medical implants as well as surgical instruments. Further, the storage system my store medical implants and instruments of other types of surgery as well.

In one example surgical application, screws of up to 90 mm may be included in the set of screws. The storage system may have sizing limitation that only allow for up to 60 mm screws to be stored in the rack of the storage system because there is not additional room in a configured set to make the rack taller. Such a problem may occur with storage systems for use with other types of medical implants. Embodiments will be described that include various aspects to overcome this problem of storing long screws in a size limited storage system.

For screws that are longer than what the rack can accommodate, one or more drawers will be placed in the storage system in a way that uses space below shorter screws hung vertically in the rack. These drawers slide in an out of the storage system. If more than one drawer is used, then they may interlock with one another so that they slide in and out of the storage system as a fixed single unit. The drawers are locked in place by a drawer locking mechanism that is automatically engaged and released when the storage system lid is closed or opened. The locking mechanism secures the drawers inside the storage system when the storage system is not in use and during transit.

FIGS. 1A-1E illustrate top perspective, top, drawer side, latch side, and bottom perspective view of a storage system 100. The storage system 100 may include a lid 102 with a handle 112. The lid 102 covers screws 190 that are stored in the rack 116. The lid 102, when closed, traps the screws 190 in the rack 116 to prevent them from coming out of the rack 116. The lid 102 may have plurality of slots 186 that allow for cleaning and/or sterilization of the storage system 100 and may also provide some visibility to the screws 190 stored in the storage system 100. The lid 102 is attached to hinges 110 that allow for the lid 102 to be opened and closed. The hinges 110 are attached to a drawer side 108 of the storage system 100. The lid 102 may be locked into place by a latch 114 when the lid 102 is closed. The latch 114 may be attached to the latch side 106 of the storage system 100.

Figure 1F:
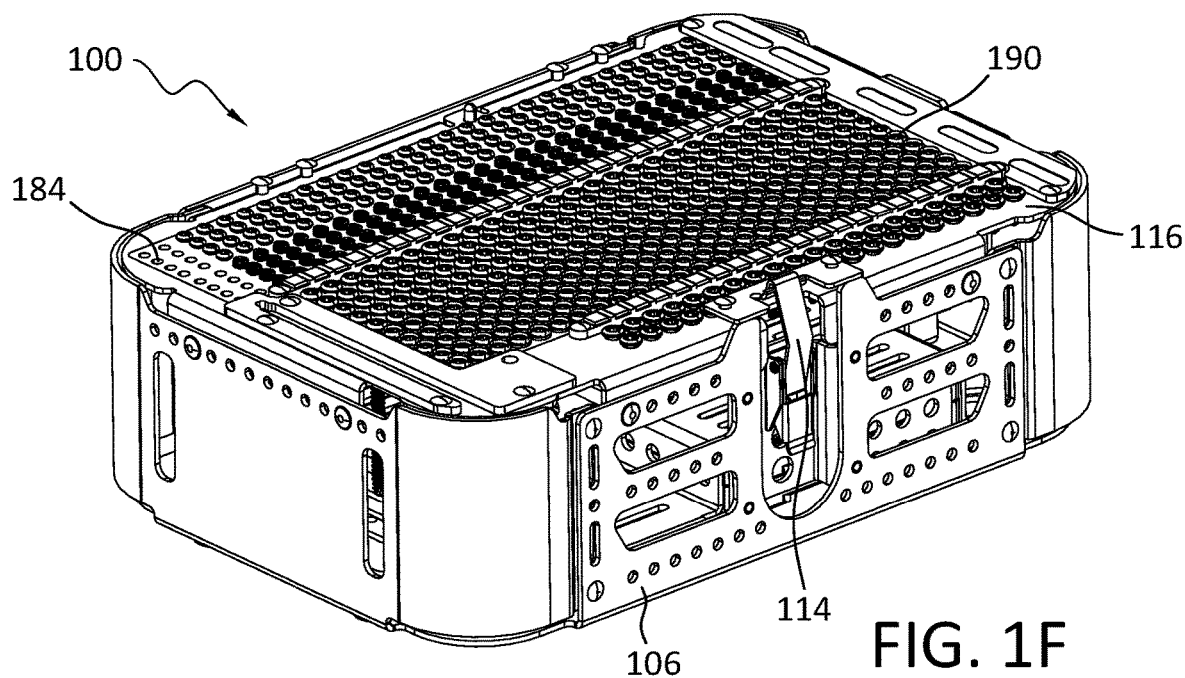
FIG. 1F illustrates a top perspective view of the storage system with the lid removed.

FIG. 1F illustrates a top perspective view of the storage system 100 with the lid 102 removed. The storage system 100 includes the rack 116 that hold the screws 190. The rack 116 has a plurality of rack screw holes 184 that receive and hold the screws 190. The screws 190 hang in the rack screw holes 184 of the rack 116 and extend towards the bottom 104. The screws are shown as being organized by size, with the longer screws 190 on a first side of the rack 116 and the shorter screws 190 on a second side of the rack 116, with size of the screw progressively decreasing from the first side to the second side. Because of this progression there is space between the ends of the shorter screws and the bottom 104 that is capable of accepting drawers that may be used to store longer screws.

The bottom 104 may also have a plurality of small holes and large holes in order to facilitate cleaning and/or sterilization of the storage system 100.

Figure 2A:
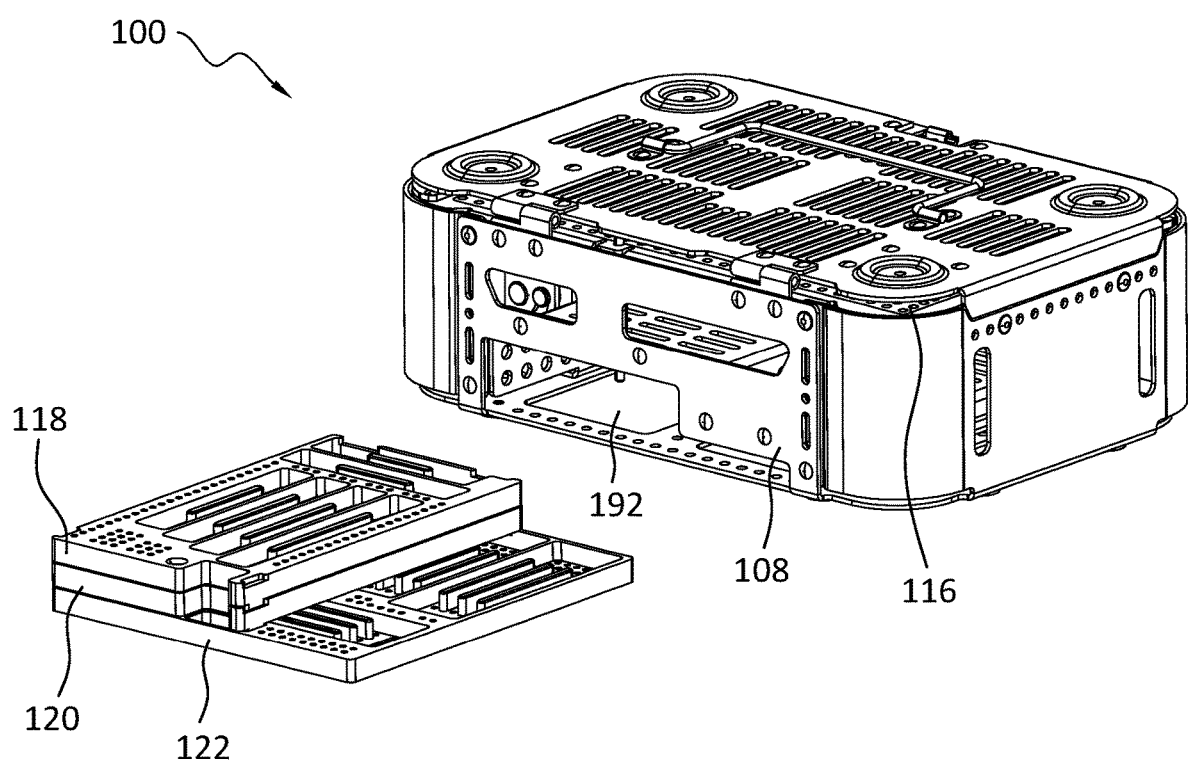
FIG. 2A illustrates a perspective view of the storage system with the drawers removed as a unit.
Figure 2B:
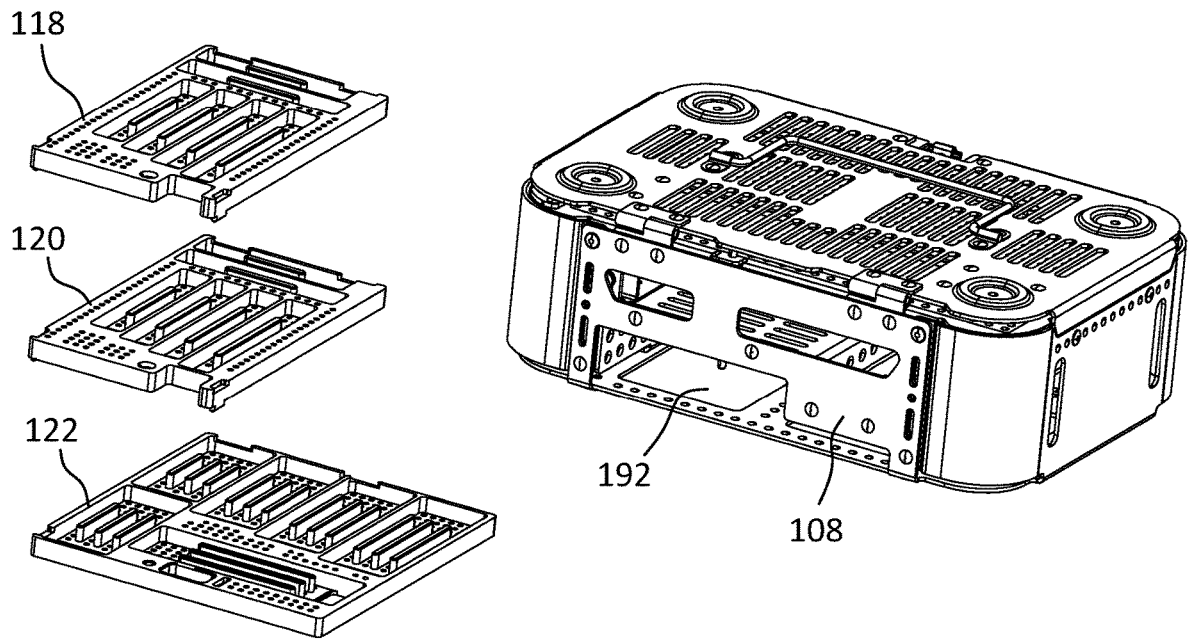
FIG. 2B illustrates a perspective view of the storage system with the drawers removed and separated vertically.
Figure 2C:
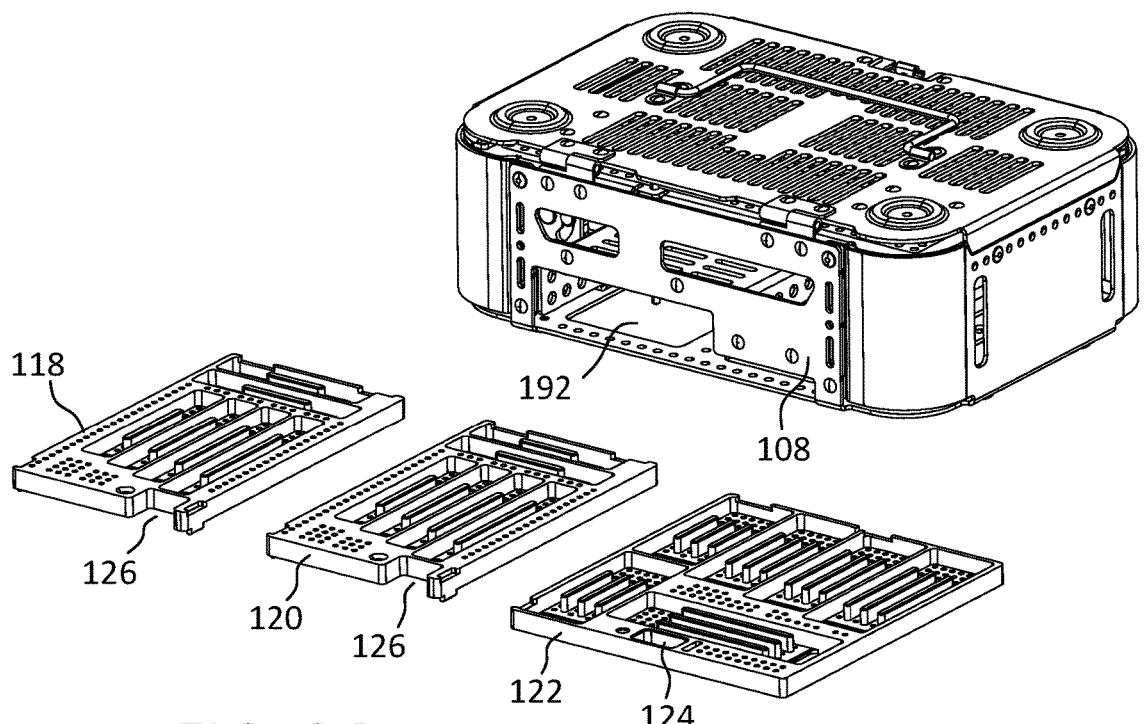
FIG. 2C illustrates a perspective view of the storage system with the drawers removed and separated horizontally.

The storage system 100 may include three drawers including a top drawer 118, a middle drawer 120, and a bottom drawer 122. FIG. 2A illustrates a perspective view of the storage system 100 with the drawers removed as a unit. FIG. 2B illustrates a perspective view of the storage system 100 with the drawers removed and separated vertically. FIG. 2C illustrates a perspective view of the storage system 100 with the drawers removed and separated horizontally. The drawer side 108 is shaped to form a drawer opening 192 that allows the drawers to be slid in and out of the storage system 100.

Figure 3A:
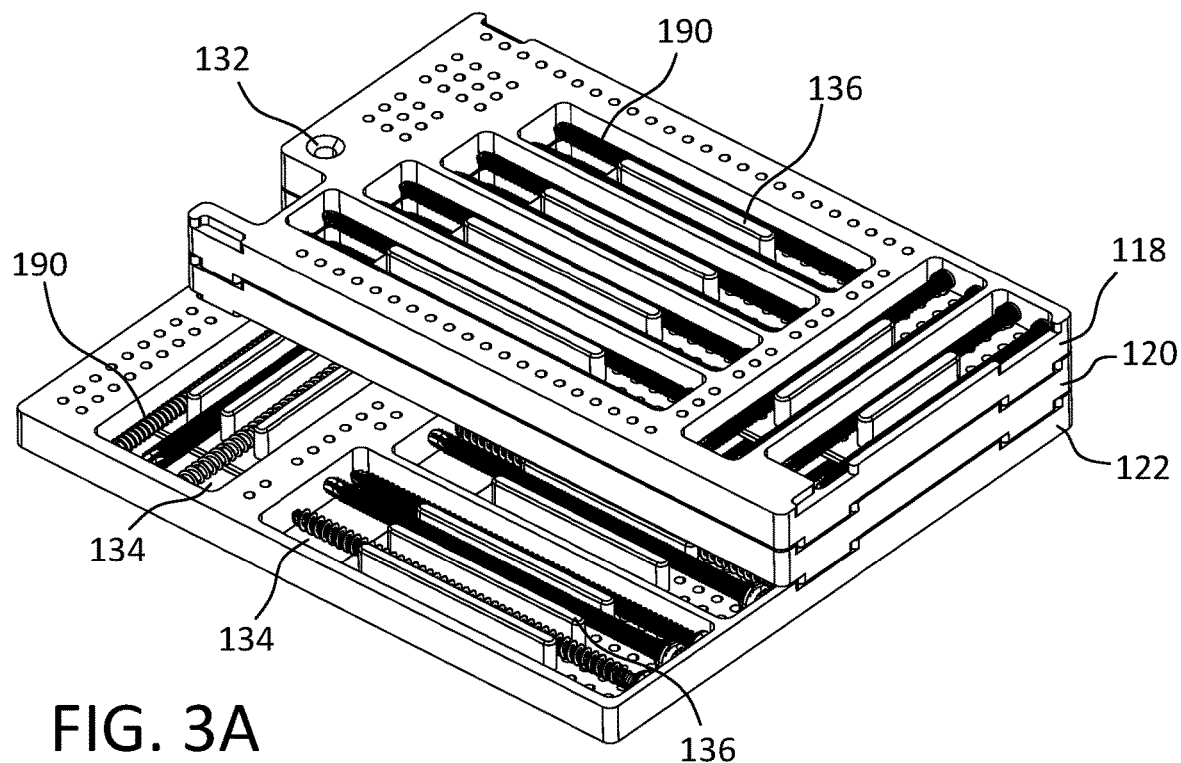
FIG. 3A illustrates a perspective view of the top drawer, middle drawer, and bottom drawer together.
Figure 3B:
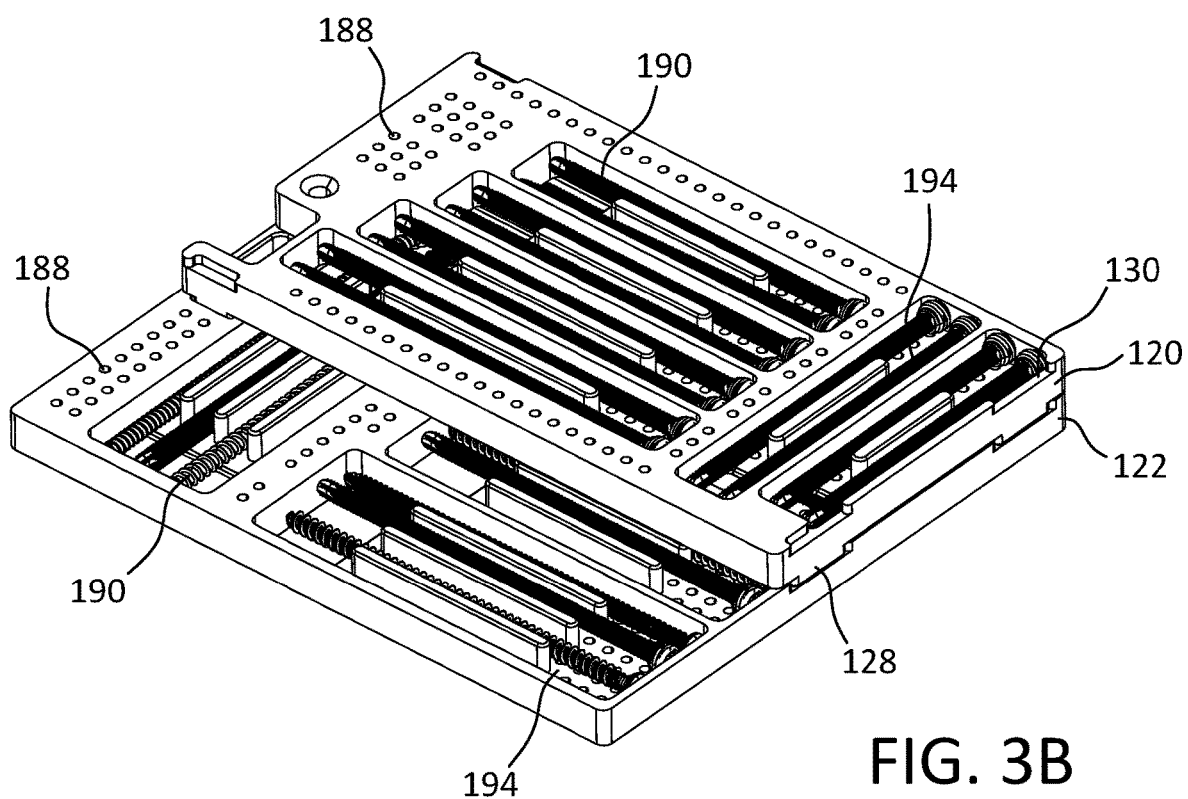
FIG. 3B illustrates a perspective view of the middle drawer and bottom drawer together.
Figure 3C:
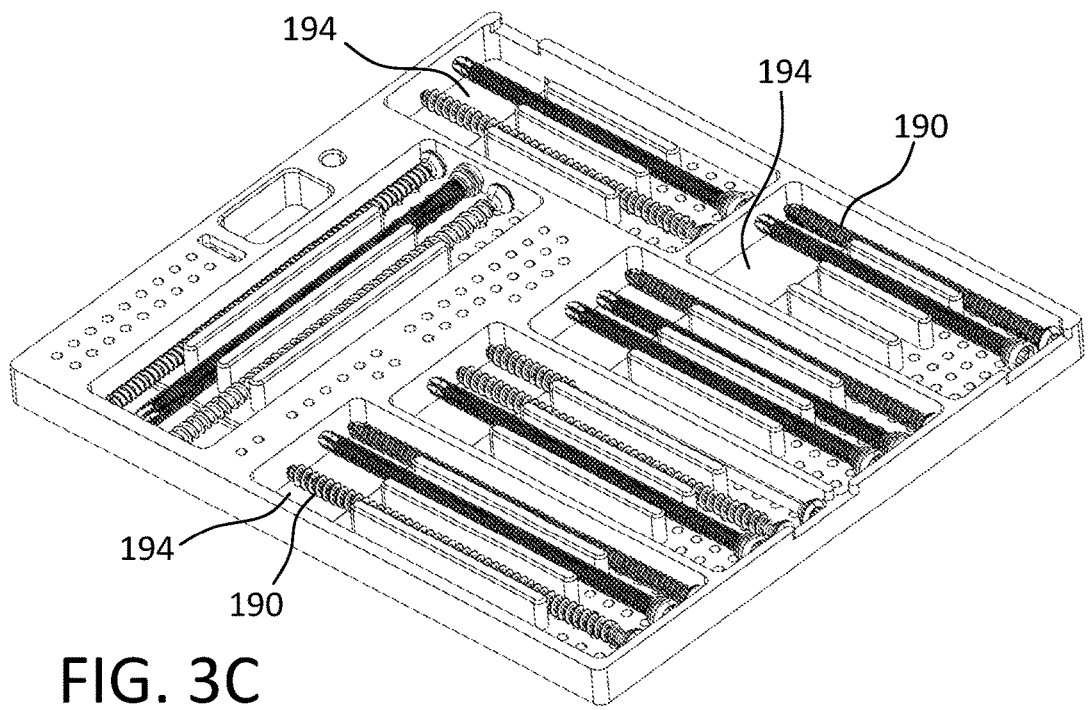
FIG. 3C illustrates a perspective view of bottom drawer.

FIG. 3A illustrates a perspective view of the top drawer 118, middle drawer 120, and bottom drawer 122 together. FIG. 3B illustrates a perspective view of the middle drawer 120 and bottom drawer 122 together. FIG. 3C illustrates a perspective view of bottom drawer 122. A plurality of screws 190 are stored horizontally in the top drawer 118, middle drawer 120, and bottom drawer 122. The direction of the screws 190 stored in the drawers is substantially perpendicular to the screws 190 stored in the rack 116. The drawers are sized to store screws 190 that are too long to be stored using the rack 116. In the example described above, this may include screw that are from 65 mm to 90 mm with lengths in 5 mm increments. Because the screws 190 are stored horizontally, they are not subject to the limitations of the rack 116. Each of top drawer 118, middle drawer 120, and bottom drawer 122 include a plurality of screw storage slots 194. The screw storage slots 194 hold one or more screws 190. The screw storage slots 194 may also include screw separators 136 that separate adjacent screws 190 in the screw storage slots 194. This prevents adjacent screws 190 from contacting one another to prevent the store screws 190 from damaging one another. The screw storage slots 194 are sized according the screws 190 that will be stored in the screw storage slots 194. Further, the screw storage slots 194 and hence the screws 190 stored in the screw storage slots 194, may be oriented in one of two substantially perpendicular directions that align with the outer edges of the drawers. Further, if needed, the screw storage slots 194 may be oriented diagonally in the drawers to accommodate long screws 190. The screw storage slots 194 may also include drawer slot opening 134 that is an opening in the bottom of the drawer at one end of the screws 190. The drawer slot opening 134 allows a user to push down on one end of the screws 190 adjacent the drawer slot opening 134 so that the other end of the screws 190 arises out of the screw storage slots 194 for easy gripping by the user.

The drawers may include drawer tabs 128 and drawer notches 130. The drawer tab 128 of one drawer engages the drawer notch 130 of the adjacent drawer. This caused the top drawer 118, middle drawer 120, and bottom drawer 122 to slide in and out of the storage system 100 as a single unit when they are stacked one on top of the other. While the drawer tab 128 and drawer notch 130 are shown on the edge of the drawers, they may be located elsewhere on the drawers and take other shapes that facilitate the engagement between the stacked drawers. This engagement allows a user of the storage system 100 to remove and insert the drawers all at once because they are fixed to one another. Further, this means that the drawer locking mechanism that will be described below only needs to engage the top drawer 118 because the drawer tabs 128 and drawer notches 130 keep the top drawer 118, middle drawer 120, and bottom drawer 122 together as a unit. The top drawer 118 may include latch opening 132 that engages the drawer locking mechanism to keep the drawers in the storage system 100.

The bottom drawer 122 is shown as being larger than top drawer 118 and middle drawer 120. This allows for the bottom drawer 122 to extend under longer screws 190 in the rack 116 to provide more storage space. Also the middle drawer 120 and bottom drawer 122 are shown as having the same size, but they could be different sizes as well. Any number of drawers that fit in the storage system 100 may be used with the same or different sizes.

The storage system 100 includes a drawer case 138. The drawers slide in and out of the drawer case 138. The drawer case 138 is located adjacent the drawer side 108 of the storage system 100. The drawer case 138 is also located under the shorter screws 190 where there is room for the drawers.

The bottom drawer 122 may have a grab opening 124 that allows the user to grab the bottom drawer 122 and pull it out of the storage system 100 along with the top drawer 118 and the middle drawer 120. Further, the top drawer 118 and middle drawer 120 may have a grab notch 126 that allows for the user to grab the grab opening 124 in the bottom drawer 122.

Figure 4A:
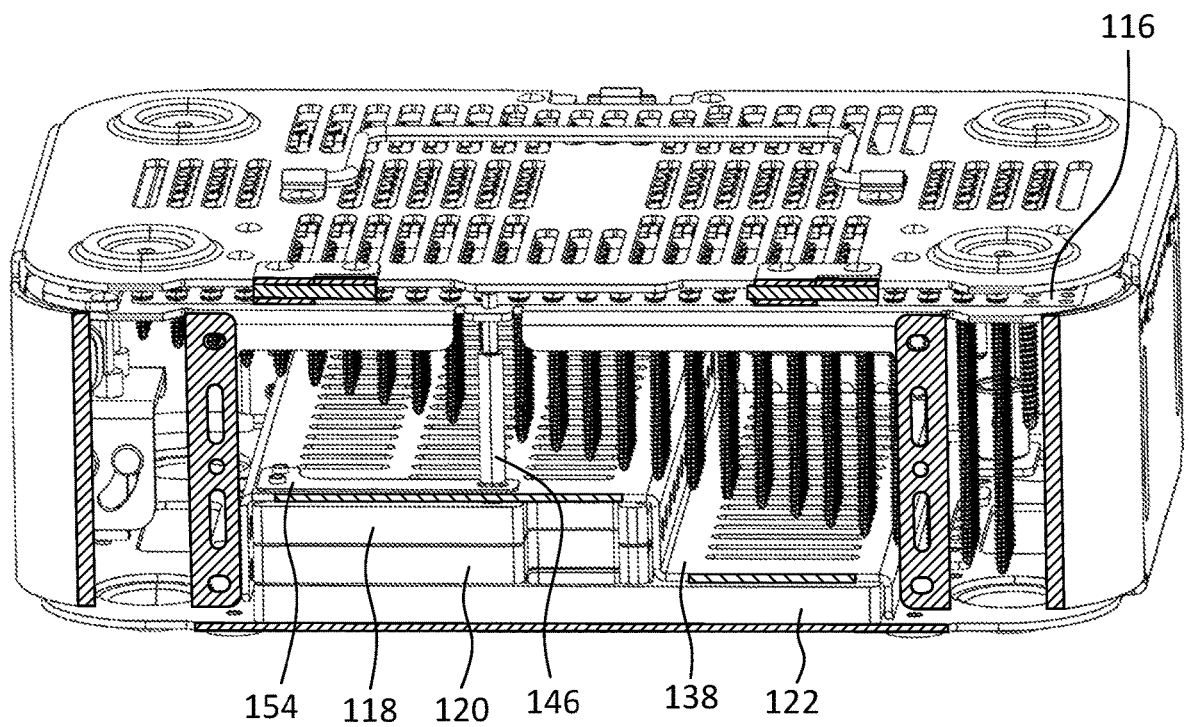
FIGS. 4A-4D illustrate various cross-sectional views the storage system illustrating the drawer locking mechanism.
Figure 4B:
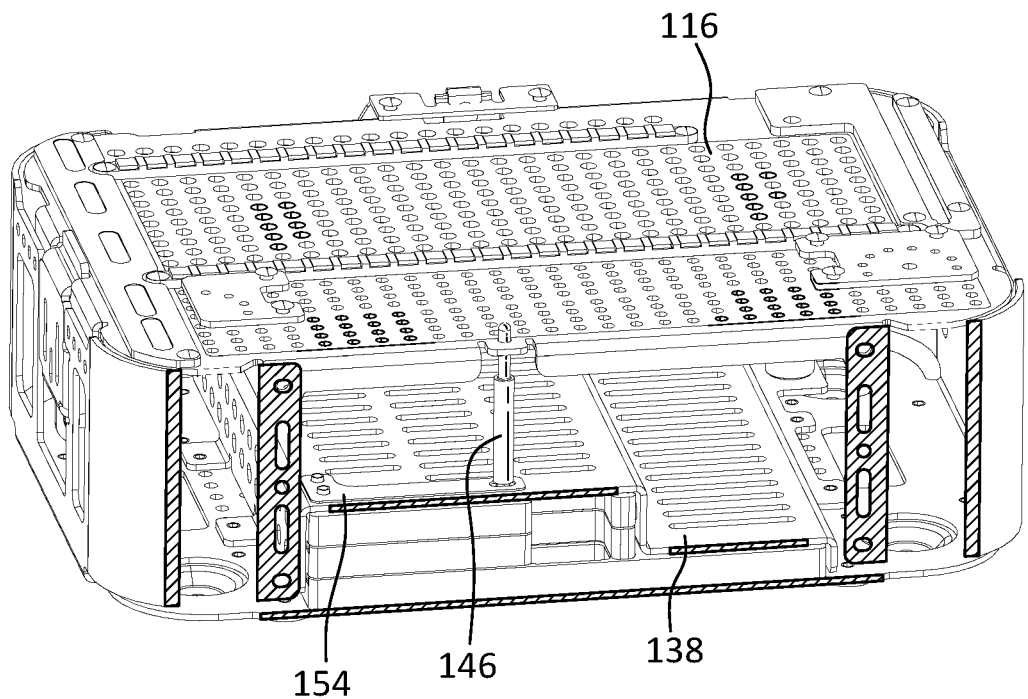
Figure 4C:
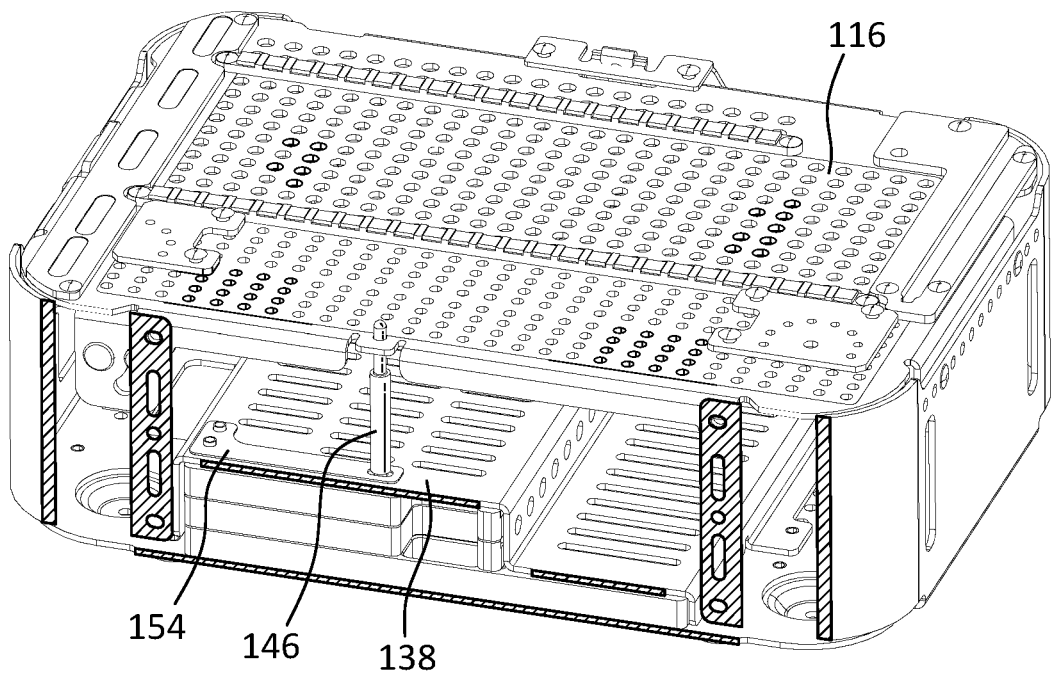
Figure 4D:
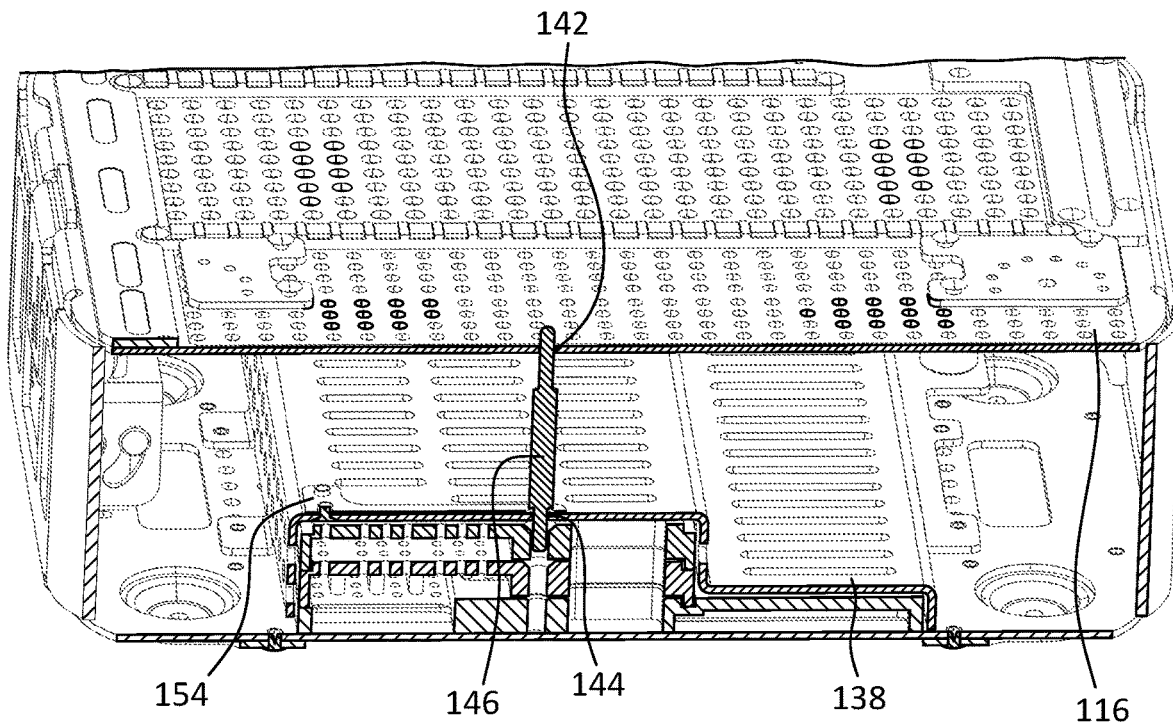
Figure 4E:
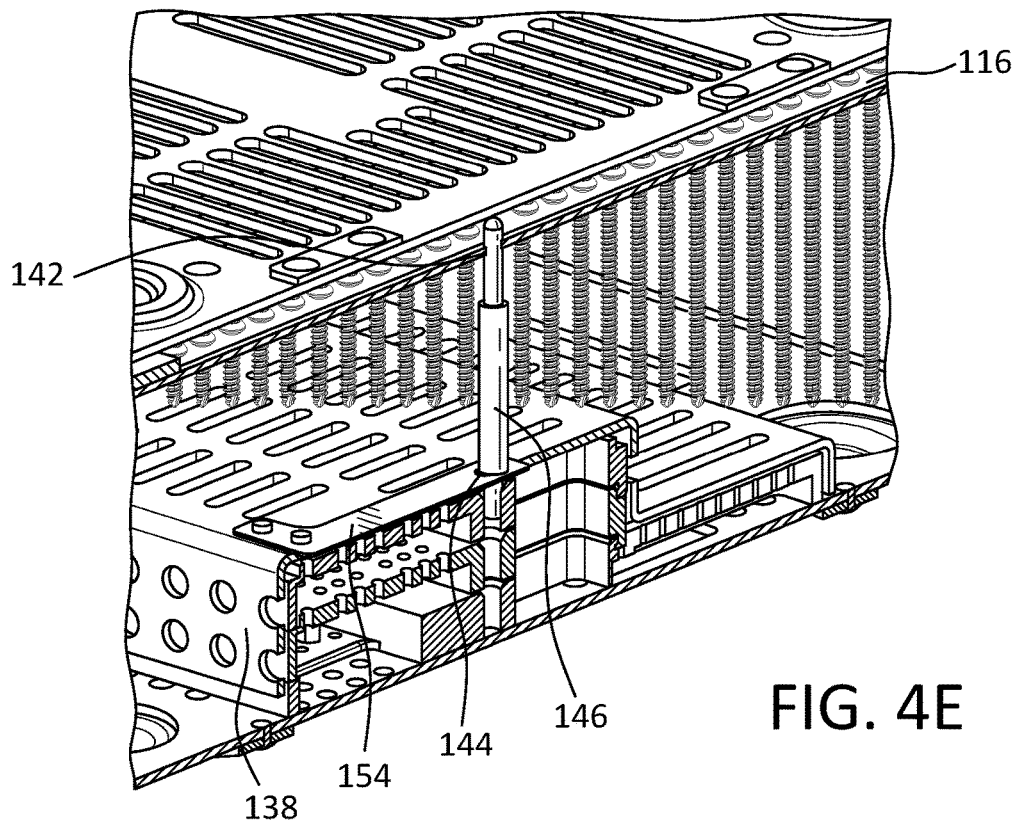
FIG. 4E illustrates a cross-sectional view of the storage system with the drawer locking mechanism in the locked position.
Figure 4F:
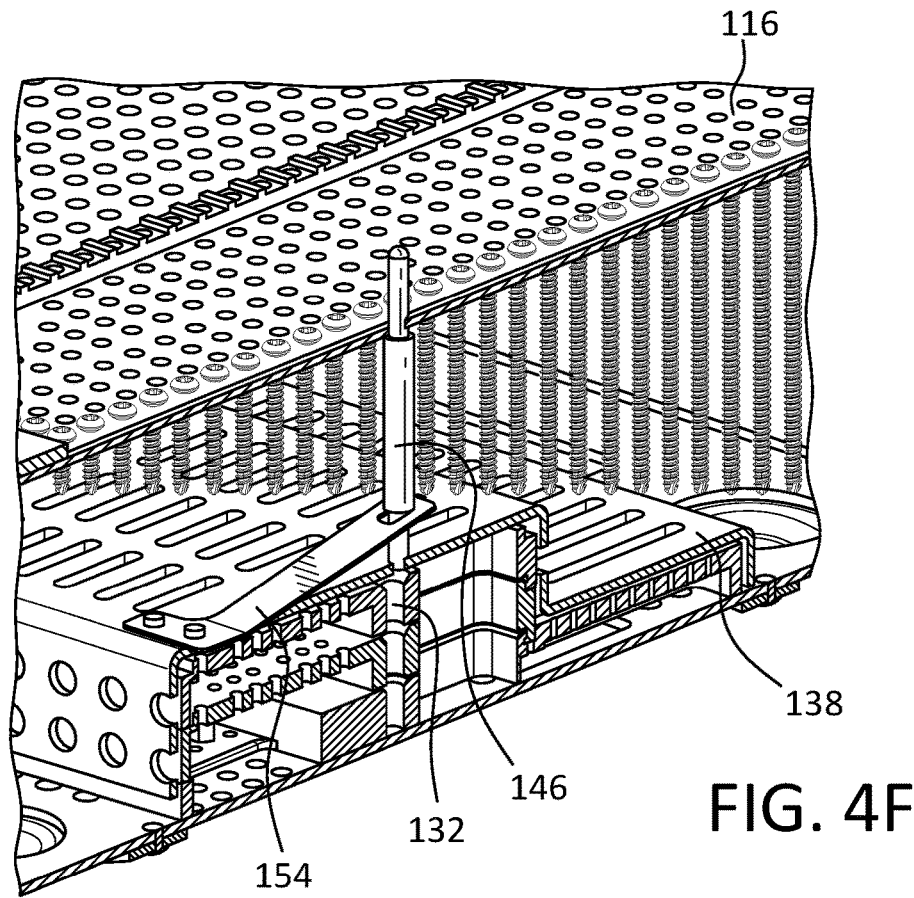
FIG. 4F illustrates a cross-sectional view of the storage system with the drawer locking mechanism in the unlocked position.
Figure 5A:
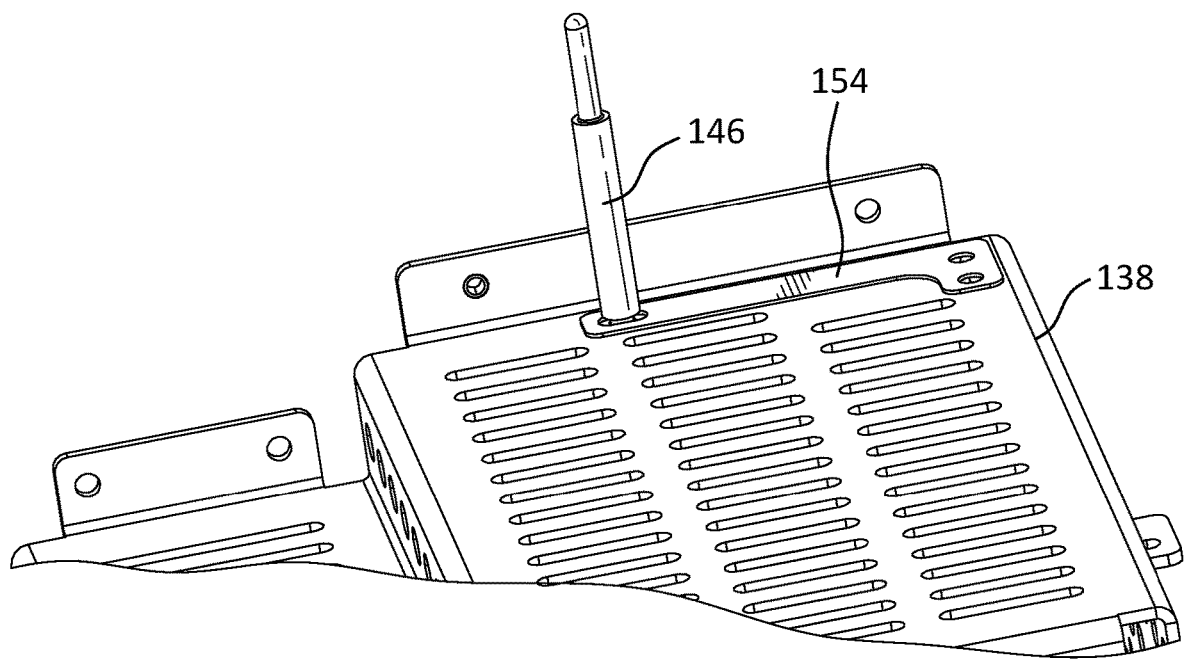
FIG. 5A illustrates the drawer locking mechanism attached to the drawer case.
Figure 5B:
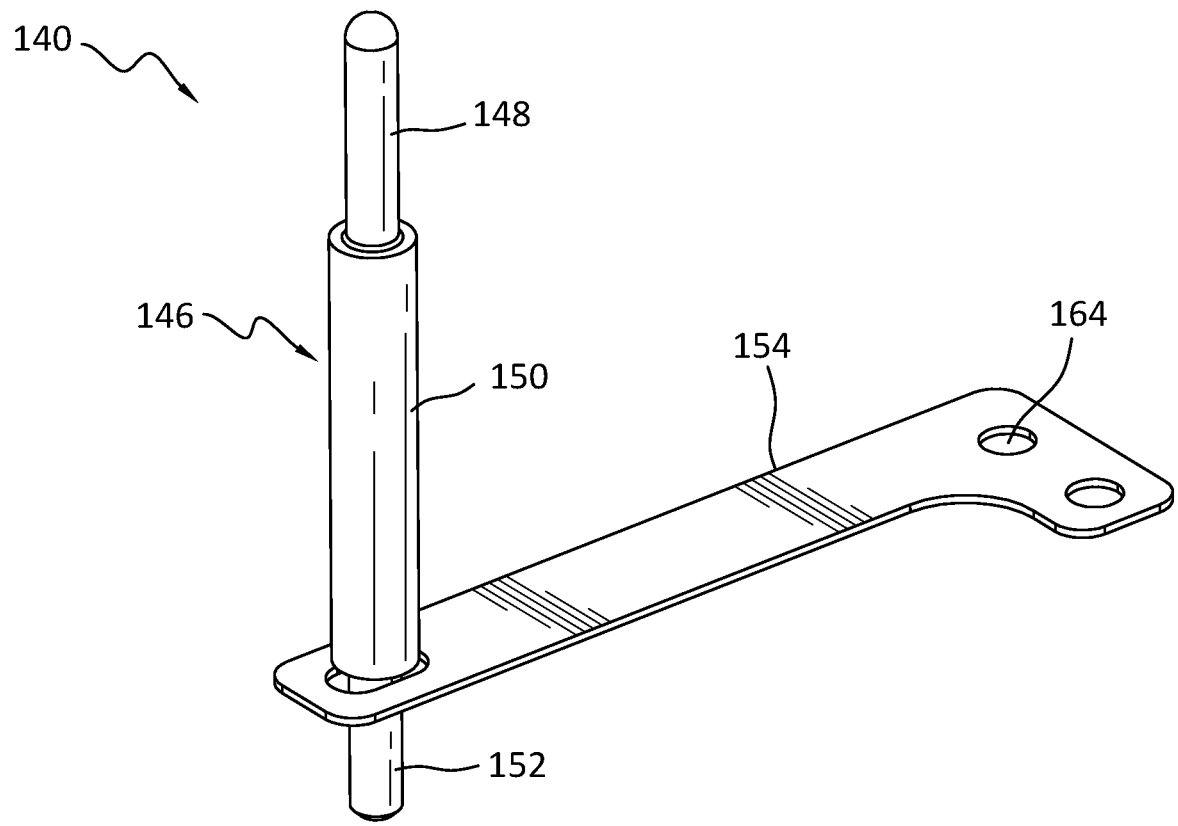
FIG. 5B illustrates drawer locking mechanism.

FIGS. 4A-4D illustrate various cross-sectional views the storage system 100 illustrating the drawer locking mechanism 140. FIG. 4E illustrates a cross-sectional view of the storage system 100 with the drawer locking mechanism 140 in the locked position. FIG. 4F illustrates a cross-sectional view of the storage system 100 with the drawer locking mechanism 140 in the unlocked position. FIG. 5A illustrates the drawer locking mechanism 140 attached to the drawer case 138. FIG. 5B illustrates drawer locking mechanism 140. The drawer locking mechanism 140 locks the drawers in the storage system 100 when the lid 102 is closed. Further, when the lid 102 is opened, the drawer locking mechanism 140 disengages from the drawers to allow the drawers to be removed from the storage system 100. The drawer locking mechanism 140 may include a drawer latch and a biasing mechanism.

Figure 6A:
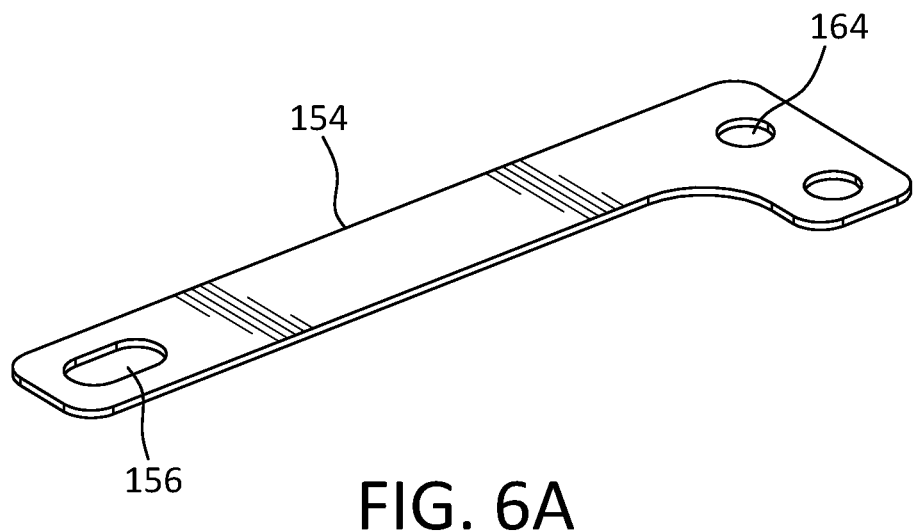
FIG. 6A illustrates a first embodiment of the leaf spring.

In one embodiment, the drawer locking mechanism 140 may include a drawer latch 146 and a leaf spring 154. FIG. 6A illustrates a first embodiment of the leaf spring 154. The leaf spring 154 is attached to the drawer case 138 via leaf spring attachment holes 164. The leaf spring 154 is configured to provide an upward bias (based upon the orientation of the figures). The leaf spring 154 has a leaf spring opening 156 near its end. The leaf spring opening 156 engages the drawer latch 146 so that the leaf spring 154 can apply an upward bias force on the drawer latch 146. The leaf spring 154 is illustrated as having a generally rectangular L-shape, but the leaf spring 154 may take on other shapes as well.

Figure 7A:
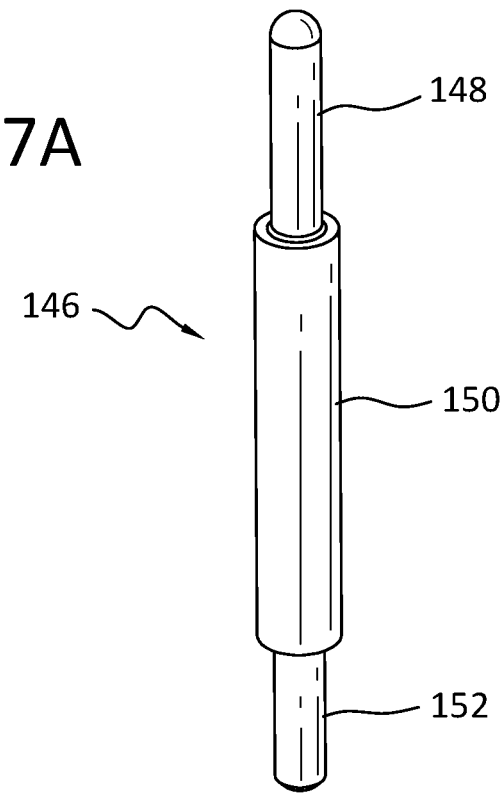
FIG. 7A illustrates a first embodiment of the drawer latch.

FIG. 7A illustrates a first embodiment of the drawer latch 146. The drawer latch 146 has a generally cylindrical shape and includes an upper drawer latch 148, lower drawer latch 152, and a drawer latch body 150. The upper drawer latch 148 extends through the rack latch opening 142 in the rack 116. The rack latch opening 142 guides the upper drawer latch 148 into contact with the lid 102 and limits the motion of the drawer latch 146 to a generally up and down direction. The upper drawer latch 148 comes into contact with the lid 102 as the lid 102 is opened and closed.

The lower drawer latch 152 extends through the leaf spring opening 156. The leaf spring opening 156 may have an elongated shape in order to accommodate drawer latch body 150 as the leaf spring 154 biases the drawer latch 146 upwards and as the lid 102 presses the drawer latch 146 downwards. The leaf spring opening 156 is shown as having an oval shape, but other shapes and sizes are possible that allow for the leaf spring 154 to bias the drawer latch 146 without binding. The lower drawer latch 152 further extends further through a drawer case latch opening 144. The drawer case latch opening 144 guides the lower drawer latch 152 into the latch opening 132 and limits the motion of the drawer latch 146 to a generally up and down direction.

The drawer latch body 150 has a larger diameter than upper drawer latch 148 and lower drawer latch 152. The size of the drawer latch body 150 is selected to be larger than leaf spring opening 156 so that the leaf spring 154 can apply an upward bias force on the drawer latch body 150 and hence the drawer latch 146. Also, the upper edge of the drawer latch body 150 provides a stopping surface against the rack 116 to limit the motion of the drawer latch 146 and to capture the drawer latch 146 between the rack 116 and the drawer case 138. Other structures may be used instead of the drawer latch body 150 to limit the movement of the drawer latch 146 and to be biased by the leaf spring 154. For example, upper and lower donut shaped structures may be used.

When the lid 102 is open, the leaf spring 154 biases the drawer latch 146 upward so that lower drawer latch 152 withdraws from the latch opening 132. This now allows a user to grip the drawers and to pull them out. When the lid 102 is closed, the lid 102 presses the upper drawer latch 148 downward in opposition to the biasing force of the leaf spring 154 and drives the lower drawer latch 152 into the latch opening 132 of the top drawer 118. This will lock the drawers in place. The drawers act as a unit because of the drawer tabs 128 and drawer notches 130 and allow for the whole set of drawers to be locked in place via the insertion of the lower drawer latch 152 into the latch opening 132 of the top drawer 118.

Figure 6B:
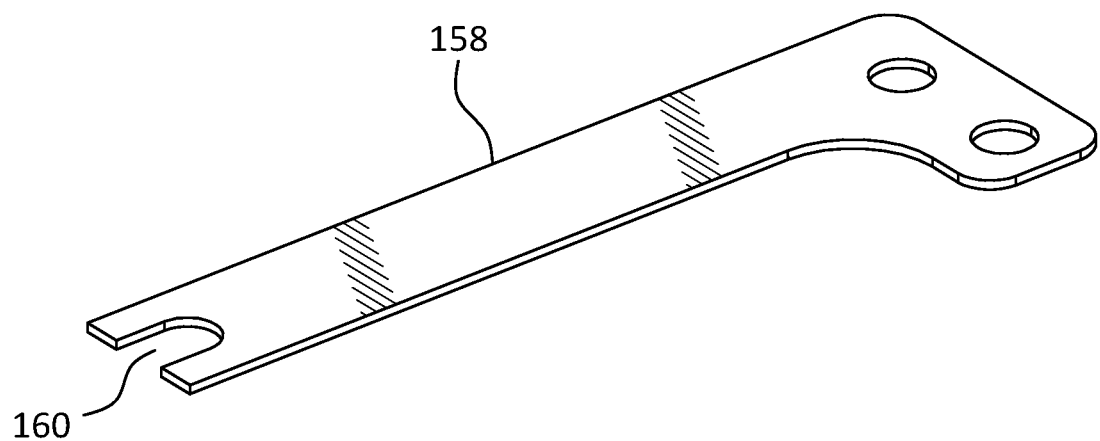
FIG. 6B illustrates a second embodiment of the leaf spring.
Figure 6C:
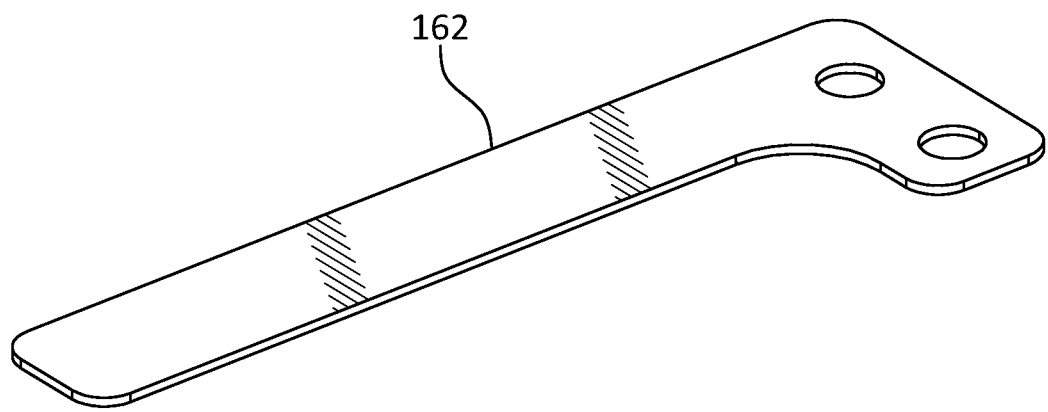
FIG. 6C illustrates a third embodiment of the leaf spring.

FIG. 6B illustrates a second embodiment of the leaf spring 158. The leaf spring 158 includes a leaf spring fork opening 160 that engages the lower drawer latch 152 and the drawer latch body 150 of the drawer latch 146. FIG. 6C illustrates a third embodiment of the leaf spring 158. The leaf spring 158 does not include any sort of opening at its end. Instead, the end of the leaf spring 162 engages a lower edge of drawer latch body 150 in order to bias the drawer latch 146 upwards.

The leaf spring 154 can take on other configurations as well as long as they provide sufficient biasing force to the drawer latch 146. Further, the leaf spring 154 may be replaced by other biasing mechanisms, for example, a coil spring. Any such biasing mechanism will provide sufficient biasing force and fit within the space constraints of the storage system 100.

Figure 7B:
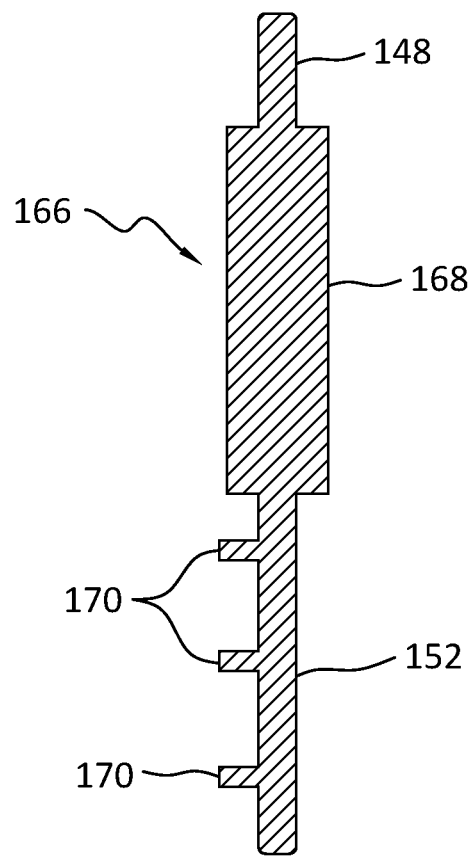
FIG. 7B illustrates a second embodiment of a drawer latch that includes a drawer latch body and drawer latch protrusions.

FIG. 7B illustrates a second embodiment of a drawer latch 166 that includes a drawer latch body 168 and drawer latch protrusions 170. The drawer latch 166 is shown as having three drawer latch protrusions 170, but the number of protrusions may match the number of drawers in the storage system 100. The drawer latch protrusion 170 are configured to engage slots on an upper edge of each of the drawers. The drawer latch body 168 provides the same function as drawer latch body 150 described above. In this case, the locking mechanism may be situated at one of the sides of the drawers rather than the front of the drawer to allow drawers to slide out of the storage system 100. When the drawer latch 166 is used, the drawer tabs 128 and drawer notches 130 are not needed to lock the drawers together as a single unit.

Figure 7C:
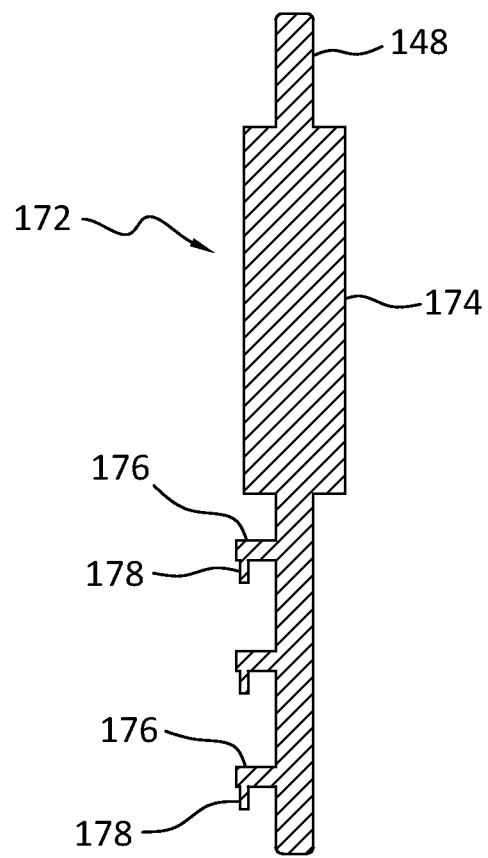
FIG. 7C illustrates a third embodiment of a drawer latch that includes drawer latch body, drawer latch protrusions, and drawer latch pins.

FIG. 7C illustrates a third embodiment of a drawer latch 172 that includes drawer latch body 174, drawer latch protrusions 176, and drawer latch pins 178. The drawer latch pin 178 extend downward from the drawer latch protrusions 176. The drawer latch 166 is shown as having three drawer latch protrusions 176 and drawer latch pins 178, but the number of drawer latch protrusion 176 and drawer latch pin 178 may match the number of drawers in the storage system 100. The drawer latch pins 178 are configured to engage holes on an upper edge of each of the drawers. The drawer latch body 174 provides the same function as drawer latch body 150 described above. In this case, the locking mechanism may be situated at one of the sides of the drawers other than the front of the drawer to allow drawers to slide out of the storage system 100. When the drawer latch 172 is used, the drawer tabs 128 and drawer notches 130 are not needed to lock the drawers together as a single unit. The drawer latch 146 can take on other configurations as well as long as they engage at least one drawer to prevent the drawers from sliding out.

In another embodiment of the drawer locking mechanism, the drawer latch may slide in front of the top drawer (i.e., rather than into the latch opening) to prevent the top drawer from being slid out of the storage system 100. Further, the drawer locking mechanism is illustrated as being located at the front of the drawers by the drawer side 108, but it may be placed in other locations relative to the drawers.

Figure 8A:
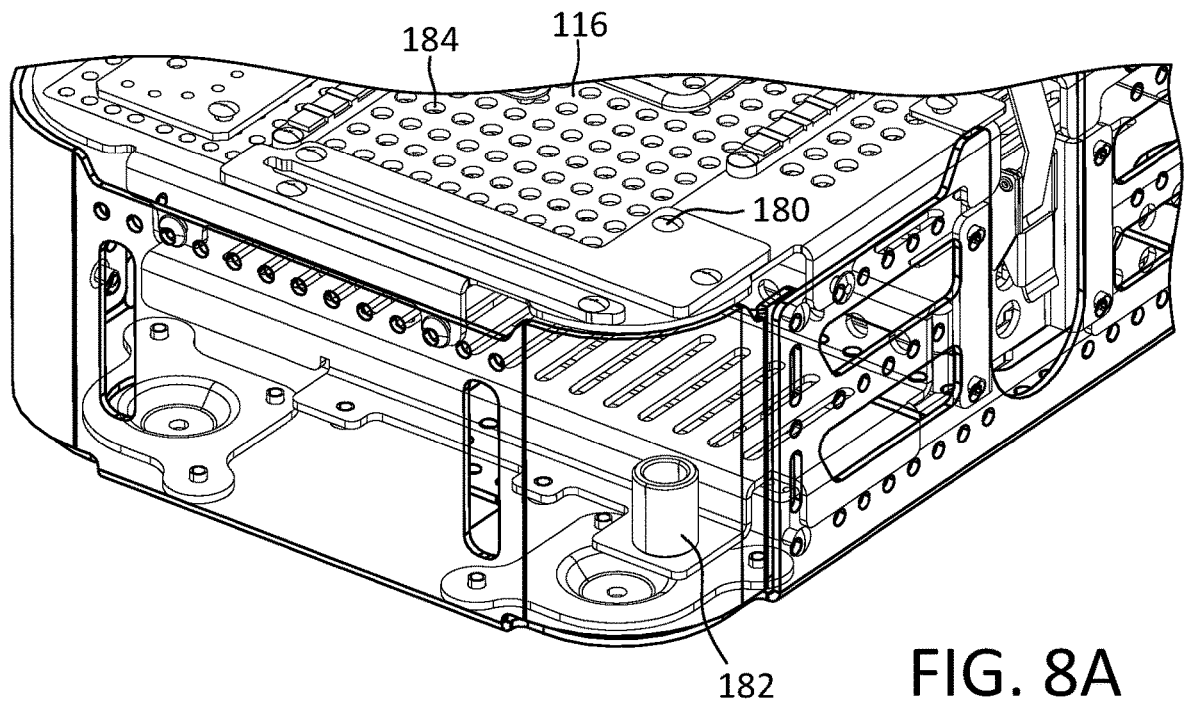
FIGS. 8A-C illustrate various views of a screw loading assembly.
Figure 8B:
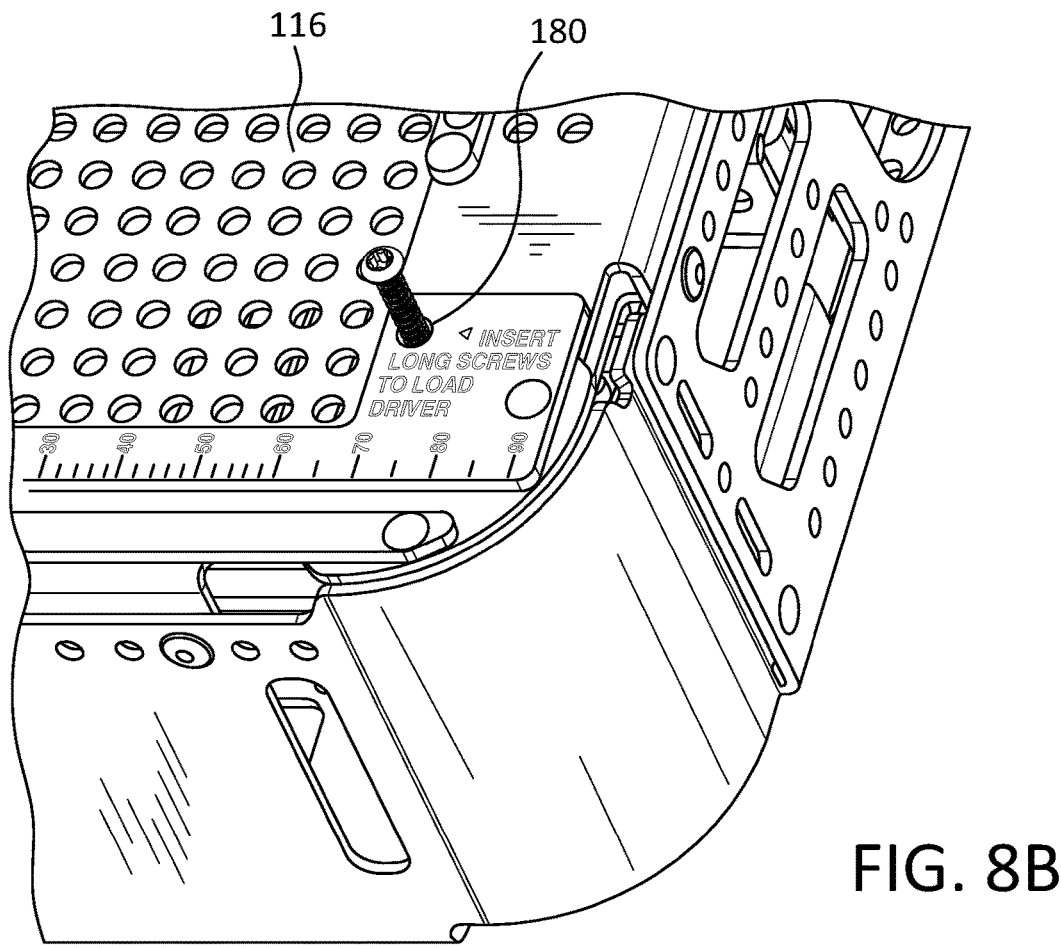
Figure 8C:
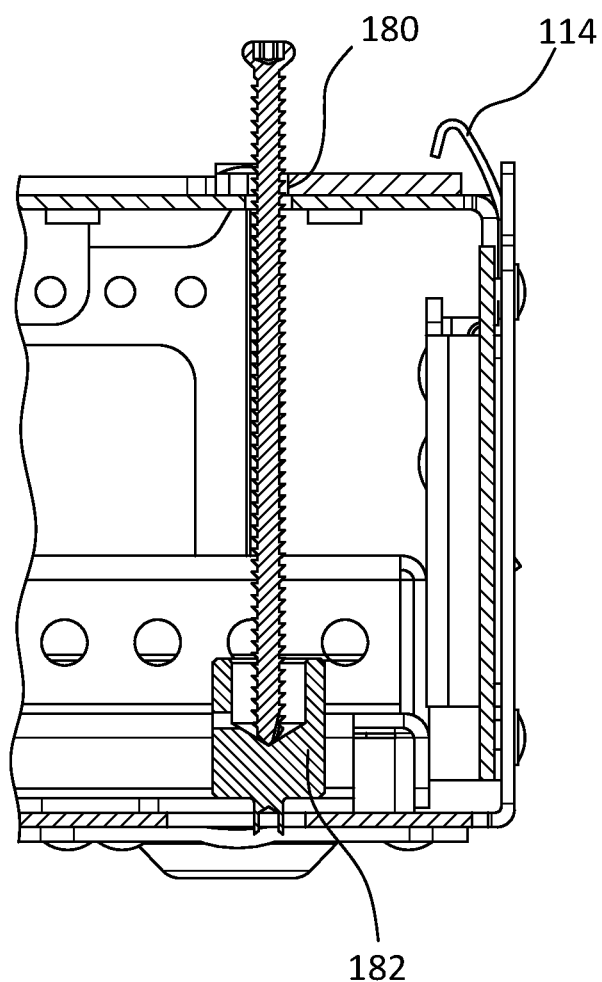

FIGS. 8A-C illustrate various views of a screw loading assembly. The screw loading assembly includes rack screw loading hole 180 and screw loading base 182. The rack screw loading hole 180 is a hole in the rack 116 that is aligned with the screw loading base 182. The screw loading base 182 includes an opening to capture the tip of a screw 190 inserted into the rack screw loading hole 180. The bottom of the opening in the screw loading base 182 may have a conical shape to direct the tip of the screw 190 to the center of the screw loading base 182. A user may place a long screw 190 into the screw loading assembly and then engage a head of the screw 190 with a driver. Then the user can remove the screw using the driver and then place the screw in its intended location. The screw loading assembly makes loading a screw onto a driver easier.

Drain holes 188 are located throughout the storage system 100 to facilitate cleaning and/or sterilization of the storage system 100. The drain holes 188 are found for example on the top drawer 118, middle drawer 120, bottom drawer 122, bottom 104, latch side 106, drawer side 108, etc.

The foregoing disclosure provides illustration and description, but is not intended to be exhaustive or to limit the aspects to the precise form disclosed. Modifications and variations may be made in light of the above disclosure or may be acquired from practice of the aspects.

Unless stated otherwise, terms such as "first" and "second" are used to arbitrarily distinguish between the elements such terms describe. Thus, these terms are not necessarily intended to indicate temporal or other prioritization of such elements.

While each of the embodiments are described above in terms of their structural arrangements, it should be appreciated that the aspects also cover the associated methods of using the embodiments described above.

Even though particular combinations of features are recited in the claims and/or disclosed in the specification, these combinations are not intended to limit the disclosure of various aspects. In fact, many of these features may be combined in ways not specifically recited in the claims and/or disclosed in the specification. Although each dependent claim listed below may directly depend on only one claim, the disclosure of various aspects includes each dependent claim in combination with every other claim in the claim set. A phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

No element, act, or instruction used herein should be construed as critical or essential unless explicitly described as such. Also, as used herein, the articles "a" and "an" are intended to include one or more items, and may be used interchangeably with "one or more." Furthermore, as used herein, the terms "set" and "group" are intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," and/or the like are intended to be open-ended terms. Further, the phrase "based on" is intended to mean "based, at least in part, on" unless explicitly stated otherwise.

The invention claimed is:

1. A storage system, comprising:
    a lid;
    a bottom side of the storage system opposite the lid;
    a first plurality of medical implants stored in a rack, wherein first plurality of medical implants is oriented in a first direction from the lid to the bottom side, and wherein the rack is between the lid and the bottom side of the storage system;
    a first drawer located between a portion of the first plurality of medical implants and the bottom side of the storage system, wherein the first drawer is configured to slide into and out of the storage system;
    a second plurality of medical implants stored in the first drawer, wherein the second plurality of medical implants are oriented in a second direction that is substantially perpendicular to the first direction; and
    a drawer locking mechanism configured to engage the first drawer when the lid is closed to prevent the first drawer from sliding out of the storage system and to disengage the first drawer when the lid is open to allow the first drawer to slide out of the storage system.

2. The storage system of claim 1, comprising:
    a second drawer located between the first drawer and the bottom side of the storage system.

3. The storage system of claim 2, wherein one of the first drawer and the second drawer have a tab and the other of the first drawer and the second drawer have a notch, wherein the tab and the notch are configured to engage one another to fix a position of the first drawer and the second drawer relative to one another.

4. The storage system of claim 1, wherein the drawer locking mechanism comprises:
    a drawer latch configured to engage the lid and the first drawer; and
    a biasing mechanism configured to bias the drawer latch towards the lid.

5. The storage system of claim 4, wherein the biasing mechanism is a leaf spring.

6. The storage system of claim 5, wherein the leaf spring has an opening configured to receive the drawer latch.

7. The storage system of claim 5, wherein the leaf spring has a fork opening configured to engage the drawer latch.

8. The storage system of claim 1, further comprising:
    a medical implant loading assembly comprising:
        a medical implant loading base configured to receive an end of a medical implant; and
        rack medical implant loading hole aligned with the medical implant loading base, wherein the rack medical implant loading hole is configured to receive and secure the medical implant along with the medical implant loading base.

9. The storage system of claim 1, where in the first drawer includes a drawer slot and a drawer slot opening on a bottom of the drawer slot at one end of the drawer slot.

10. The storage system of claim 1, where in the first drawer includes a drawer slot and a separator configured to separate medical devices in the drawer slot.

11. A storage system, comprising:
    a lid configured to be opened and closed;
    a bottom side of the storage system opposite the lid;
    a rack between the lid and the bottom side of the storage system, wherein the rack includes a plurality of rack screw holes;
    a first plurality of screws stored in the plurality of rack screw holes;
    a first drawer located between a portion of the first plurality of screws and the bottom side of the storage system, wherein the first drawer is configured to slide into and out of the storage system;

a second plurality of screws stored in the first drawer, wherein the second plurality of screws are oriented in a direction that is different than a direction of the first plurality of screws; and a drawer locking mechanism configured to engage the first drawer when the lid is closed to prevent the first drawer from sliding out of the storage system and to disengage the first drawer when the lid is open to allow the first drawer to slide out of the storage system.

12. The storage system of claim 11, comprising:
a second drawer located between the first drawer and the bottom side of the storage system.

13. The storage system of claim 12, wherein one of the first drawer and the second drawer have a tab and the other of the first drawer and the second drawer have a notch, wherein the tab and the notch are located to engage one another to fix a position of the first drawer and the second drawer relative to one another.

14. The storage system of claim 11, wherein the drawer locking mechanism comprises:
a drawer latch configured to engage the lid and the first drawer; and
a biasing mechanism configured to bias the drawer latch towards the lid.

15. The storage system of claim 14, wherein the biasing mechanism is a leaf spring.

16. The storage system of claim 15, wherein the leaf spring has an opening configured to receive the drawer latch.

17. The storage system of claim 15, wherein the leaf spring has a fork opening configured to engage the drawer latch.

18. The storage system of claim 11, further comprising:
a screw loading assembly comprising:
a screw loading base configured to receive an end of a screw; and
rack screw loading hole aligned with the screw loading base, wherein the rack screw loading hole is configured to receive and secure the screw along with the screw loading base.

19. The storage system of claim 11, where in the first drawer includes a drawer slot and a drawer slot opening on a bottom of the drawer slot at one end of the drawer slot.

20. The storage system of claim 11, where in the first drawer includes a drawer slot and a separator configured to separate medical devices in the drawer slot.

* * * * *